United States Patent
Lee

(10) Patent No.: US 11,591,600 B2
(45) Date of Patent: Feb. 28, 2023

(54) LONG DOUBLE-STRANDED RNA FOR RNA INTERFERENCE

(71) Applicant: OliX Pharmaceuticals, Inc., Gyeonggi-do (KR)

(72) Inventor: Dong Ki Lee, Seoul (KR)

(73) Assignee: OliX Pharmaceuticals. Inc., Gyeonggi-do (KR)

( * ) Notice: Subject to any disclaimer, the term of this patent is extended or adjusted under 35 U.S.C. 154(b) by 0 days.

(21) Appl. No.: 16/484,643

(22) PCT Filed: Feb. 12, 2018

(86) PCT No.: PCT/IB2018/000330
§ 371 (c)(1),
(2) Date: Aug. 8, 2019

(87) PCT Pub. No.: WO2018/146557
PCT Pub. Date: Aug. 16, 2018

(65) Prior Publication Data
US 2021/0285001 A1    Sep. 16, 2021

Related U.S. Application Data

(60) Provisional application No. 62/457,282, filed on Feb. 10, 2017.

(51) Int. Cl.
| | | |
|---|---|---|
| C07H 21/02 | (2006.01) | |
| C07H 21/04 | (2006.01) | |
| C12N 15/113 | (2010.01) | |
| A61K 31/7125 | (2006.01) | |
| A61K 31/713 | (2006.01) | |

(52) U.S. Cl.
CPC ........ *C12N 15/1135* (2013.01); *A61K 31/713* (2013.01); *A61K 31/7125* (2013.01); *C12N 2310/11* (2013.01); *C12N 2310/14* (2013.01); *C12N 2310/315* (2013.01); *C12N 2310/335* (2013.01); *C12N 2310/3341* (2013.01); *C12N 2310/344* (2013.01); *C12N 2310/3515* (2013.01); *C12N 2310/53* (2013.01)

(58) Field of Classification Search
CPC .................. C12N 15/1113; A61K 31/713
See application file for complete search history.

(56) References Cited

U.S. PATENT DOCUMENTS

| | | | |
|---|---|---|---|
| 5,837,258 A | 11/1998 | Grotendorst | |
| 7,078,196 B2 | 7/2006 | Tuschl et al. | |
| 7,691,995 B2 * | 4/2010 | Zamore | C12N 15/8509 536/24.5 |
| 7,691,997 B2 | 4/2010 | Khvorova et al. | |
| 7,700,541 B2 | 4/2010 | Tanaka et al. | |
| 8,410,260 B2 | 4/2013 | Collin-Djangone et al. | |
| 8,614,309 B2 | 12/2013 | Feinstein et al. | |
| 8,802,733 B2 | 8/2014 | Ganesan et al. | |
| 8,822,428 B2 | 9/2014 | Collin-Djangone et al. | |
| 8,980,273 B1 | 3/2015 | Clube | |
| 9,453,226 B2 | 9/2016 | Ambati et al. | |
| 9,637,742 B2 | 5/2017 | Lee | |
| 9,707,235 B1 | 7/2017 | Ambati | |
| 10,059,949 B2 | 8/2018 | Lee et al. | |
| 10,064,801 B2 | 9/2018 | Hong et al. | |
| 10,125,362 B2 | 11/2018 | Hong | |
| 10,214,744 B2 | 2/2019 | Lee | |
| 10,358,648 B2 | 7/2019 | Lee et al. | |
| 2004/0138163 A1 | 7/2004 | McSwiggen et al. | |
| 2004/0180351 A1 | 9/2004 | Giese et al. | |
| 2004/0198640 A1 | 10/2004 | Leake et al. | |
| 2004/0266707 A1 | 12/2004 | Leake et al. | |
| 2005/0119202 A1 | 6/2005 | Kreutzer et al. | |
| 2005/0282188 A1 | 12/2005 | Haeberli et al. | |
| 2006/0069050 A1 | 3/2006 | Rana | |
| 2006/0094032 A1 | 5/2006 | Fougerolles et al. | |
| 2006/0105976 A1 | 5/2006 | Soutschek et al. | |
| 2006/0134787 A1 | 6/2006 | Zamore et al. | |
| 2006/0142228 A1 | 6/2006 | Ford et al. | |
| 2006/0160123 A1 | 7/2006 | Quay | |
| 2007/0218495 A1 | 9/2007 | Birmingham et al. | |
| 2007/0275914 A1 | 11/2007 | Manoharan et al. | |
| 2008/0125386 A1 | 5/2008 | Rana et al. | |
| 2008/0188430 A1 | 8/2008 | Usman et al. | |
| 2009/0004668 A1 | 1/2009 | Chen et al. | |
| 2009/0012022 A1 | 1/2009 | Milner et al. | |
| 2009/0130751 A1 | 5/2009 | Davidson et al. | |
| 2009/0191625 A1 | 7/2009 | Khvorova et al. | |
| 2009/0208564 A1 | 8/2009 | Li et al. | |
| 2009/0286852 A1 | 11/2009 | Kariko et al. | |
| 2010/0145038 A1 * | 6/2010 | McSwiggen | C07H 21/02 536/24.5 |
| 2010/0197023 A1 | 8/2010 | Leake et al. | |
| 2010/0247540 A1 * | 9/2010 | Burns | A61K 39/3955 424/139.1 |
| 2010/0254945 A1 | 10/2010 | Ge et al. | |
| 2010/0291681 A1 | 11/2010 | Khvorova et al. | |
| 2011/0028534 A1 | 2/2011 | Shepard et al. | |
| 2011/0054160 A1 | 3/2011 | Manoharan | |
| 2011/0237647 A1 | 9/2011 | Shirasawa et al. | |
| 2011/0237648 A1 | 9/2011 | Khvorova et al. | |

(Continued)

FOREIGN PATENT DOCUMENTS

| | | |
|---|---|---|
| CN | 102719432 | 10/2012 |
| EP | 2631291 | 8/2013 |
| JP | 2012502991 | 2/2012 |
| KR | 101207561 | 12/2012 |
| WO | WO0244321 | 6/2002 |

(Continued)

OTHER PUBLICATIONS

Omi et al. (FEBS Letters, 558, 2004, 89-95).*
Anderson et al., "Incorporation of Pseudouridine into mRNA Enhances Translation by Diminishing PKR Activation", Nucleic Acids Research, vol. 38, No. 17, 2010, pp. 5884-5892.

(Continued)

*Primary Examiner* — Amy H Bowman
(74) *Attorney, Agent, or Firm* — Morgan, Lewis & Bockius LLP

(57) ABSTRACT

The present technology relates, in part, to long double-stranded RNA (dsRNA) (e.g., 30 or more base pairs) that inhibits gene expression.

19 Claims, 8 Drawing Sheets

Specification includes a Sequence Listing.

(56) References Cited

U.S. PATENT DOCUMENTS

| | | |
|---|---|---|
| 2011/0245320 A1 | 10/2011 | Vornlocher et al. |
| 2011/0251258 A1 | 10/2011 | Samarsky et al. |
| 2011/0263680 A1 | 10/2011 | Khvorova et al. |
| 2011/0269816 A1 | 11/2011 | Kaspar et al. |
| 2012/0016011 A1 | 1/2012 | Pickering et al. |
| 2012/0238017 A1 | 9/2012 | Lee et al. |
| 2013/0011922 A1 | 1/2013 | Quay et al. |
| 2013/0035368 A1 | 2/2013 | Avkin-Nachum et al. |
| 2013/0115613 A1 | 5/2013 | Madiraju et al. |
| 2013/0123342 A1 | 5/2013 | Brown |
| 2013/0131142 A1 | 5/2013 | Libertine et al. |
| 2013/0190387 A1 | 7/2013 | Feinstein |
| 2013/0273657 A1 | 10/2013 | Lee |
| 2013/0317080 A1 | 11/2013 | Rajeev et al. |
| 2013/0330824 A1* | 12/2013 | Li .................... C12N 15/111 435/375 |
| 2014/0094501 A1 | 4/2014 | Puri et al. |
| 2014/0227266 A1 | 8/2014 | Lee et al. |
| 2014/0249304 A1 | 9/2014 | Lee et al. |
| 2014/0328903 A1 | 11/2014 | Santel et al. |
| 2014/0350068 A1 | 11/2014 | Feinstein et al. |
| 2015/0111948 A1 | 4/2015 | Hong |
| 2015/0184163 A1 | 7/2015 | Wilson et al. |
| 2016/0017056 A1 | 1/2016 | Clube |
| 2016/0122764 A1 | 5/2016 | Chae et al. |
| 2016/0319278 A1 | 11/2016 | Khvorova et al. |
| 2017/0298358 A1 | 10/2017 | Lee et al. |
| 2017/0369882 A1 | 12/2017 | Khvorova et al. |

FOREIGN PATENT DOCUMENTS

| | | |
|---|---|---|
| WO | WO02055693 | 7/2002 |
| WO | WO2005062937 | 7/2005 |
| WO | WO2005079533 | 9/2005 |
| WO | WO2007002470 | 2/2007 |
| WO | WO2007128477 | 11/2007 |
| WO | WO2008109377 | 9/2008 |
| WO | WO2009020344 | 2/2009 |
| WO | WO2009029688 | 3/2009 |
| WO | WO2009029690 | 3/2009 |
| WO | WO2009078685 | 6/2009 |
| WO | WO2009105260 | 8/2009 |
| WO | WO2010033247 | 3/2010 |
| WO | WO2010090762 | 8/2010 |
| WO | WO201119887 | 9/2011 |
| WO | WO2012078536 | 6/2012 |
| WO | WO2012118911 | 9/2012 |
| WO | WO2014043291 | 3/2014 |
| WO | WO2015002513 | 1/2015 |
| WO | WO2015015498 | 2/2015 |
| WO | WO2015171641 | 11/2015 |
| WO | WO2017017523 | 2/2017 |
| WO | WO2017085550 | 5/2017 |
| WO | WO2017134525 | 8/2017 |
| WO | WO2017134526 | 8/2017 |
| WO | WO2017178883 | 8/2017 |
| WO | WO2018004284 | 1/2018 |
| WO | WO2018146557 | 8/2018 |

OTHER PUBLICATIONS

European Search Report for European Application No. 18750685.2, dated Nov. 17, 2020, 10 pages.

Omi et al., "Long-lasting RNAi activity in mammalian neurons", FEBS Letters, Elsevier, Amsterdam, NL, vol. 558, No. 1-3, 2004, pp. 89-95.

Ambati et al., "Mechanisms of Age-Related Macular Degeneration," Neuron, 75: 26-39 (2012).

Bolcato-Bellemin et al., "Sticky overhangs enhance siRNA-mediated gene silencing," PNAS, vol. 104, No. 41, pp. 16050-16055 (2007).

Bramsen et al., "Improved silencing properties using small internally segmented interfering RNAs," Nucleic Acids Research, (2007), pp. 5886-5897, vol. 35.

Bushati et al., "MicroRNAs in Neurodegeneration," Current Opin Neurobiol, 18: 292-296 (2008).

Caplen et al., "Specific inhibition of gene expression by small double-stranded RNAs in invertebrate and vertebrate systems," Proc. Natl. Acad. Sci. USA, (2001), pp. 9742-9747, vol. 98, No. 17.

Chang et al., "Structural diversity repertoire of gene silencing small interfering RNAs," Nucleic acid therapeutics, (2011), 21(3), 125-131.

Chang et al., "The design, preparation, and evaluation of asymmetric small interfering RNA for specific gene silencing in mammalian cells." Methods Mol Biol. 2013; 942:135-52.

Chang et al., "Asymmetric shorter-duplex siRNA structures trigger efficient gene silencing with reduced nonsoecific effects," Mol Ther, (2009), 17(4): 725-732.

Chiu et al., "siRNA Function in RNAi: A Chemical Modification Analysis," RNA, 9: 1034-1048 (2003).

Doench et al., "siRNAs Can Function as miRNAs," Gene Dev, 17(4): 438-442 (2003).

Doench et al., "Specificity of MicroRNA Target Selection in Translation Repression," Gene Dev, 18: 504-511 (2004).

Elbashir et al., "Duplexes of 21-nucleotide RN as mediate RNA interference in cultured mammalian cells," Nature, (2001), 411:494-498.

Elbashir et al., "Functional anatomy of siRNAs for mediating efficient RNAi in Drosophila melanogaster embryo lysate," The EMBO Journal, (2001), pp. 6877-6888, vol. 20, No. 23.

Fire, "RNA-triggered gene silencing," Trends in Genetics, (1999), vol. 15, No. 9, pp. 358-363.

Fire et al., "Potent and specific genetic interference by double-stranded RNA in Caenorhabditis elegans," Nature (1998), pp. 806-811, vol. 391.

Grimm, "Small silencing RNAs: State of the art," Advanced Drug Delivery Reviews, 61: 672-703 (2009).

Gvozdeva et al., "42- and 63-bp anti-MDR1-siRNAs bearing 2'-OMe modifications in nuclease-sensitive sites induce specific and potent gene silencing," FEBS Letters 588 (2014), pp. 1037-1043.

Gvozdeva et al., "Nuclease-resistant 63-bp trimeric siRNAs simultaneously silience three different genes in tumor cells," FEBS Letters 592 (2018), pp. 122-129.

Hammond et al., "Post-Transcriptional Gene Silencing by Double-Stranded RNA," Nature Reviews Genetics, (2001), vol. 2: 110-119.

Hong et al., "Effect of the guide strand 3'-end structure on the gene-silencing potency of asymmetric siRNA," Biochemical Journal, (2014), 461(3): 427-434.

Huang et al., "Targeting the ANGPT-TIE2 Pathway in Malignancy," Nat Rev Cancer, 10: 575-585 (2010).

Hwang, "Development of Cell-Penetrating Asymmetric Interfering RNA Targeting Connective Tissue Growth Factor," Journal of Investigative Dermatology, (2016), 136(11), 2305-2313.

Jackson et al., "Expression Profiling Reveals Off-Target Gene Regulation by RNAi," Nat Biotechnol, 21: 635-637 (2003).

Jang et al., "Gene Delivery From Polymer Scaffolds for Tissue Engineering," Expert Rev Med Devic, 1(1): 127-138 (2004).

Jeong et al., "siRNA conjugate delivery systems," Bioconjugate Chem, 20:5-14 (2009).

Jo et al., "Selection and optimization of asymmetric siRNA targeting the human c-MET gene," Mol Cell, 32:(6) 543-548 (2011).

Joshi et al., "siRNA: novel therapeutics from functional genomics," Biotechnology and Genetic Enginnering Reviews (2014) vol. 30, No. 1, pp. 1-30.

Kelly et al., "Cell Type-Specific Regulation of Angiogenic Growth Factor Gene Expression and Induction of Angiogenesis in Nonischemic Tissue by a Constitutively Active Form of Hypoxia-inducible Factor 1," Circ Res, 93: 1074-1081 (2003).

Kim et al., "Synthetic dsRNA Dicer substrates enhance RNAi potency and efficacy," Nature Biotechnology, 23: 222-226 (2005).

Kore et al., "Chemical modification of synthetic RNAi agents and in vivo delivery techniques," Curr Bioactive Compounds, 4:6-14 (2008).

(56) References Cited

OTHER PUBLICATIONS

Kubo et al., "Modified 27nt dsRNAs with Dramatically Enhanced Stability in Serum and Long-Term RNAi Activity," Oligonucleotides, 17:445-464 (2007).
Kulkarni et al., "Evidence of Off-Target Effects Associated with Long dsRNAs in Drosophila melanogaster Cell-Based Assays," Nat Methods, 3: 833-838 (2006).
Lee et al., "Asymmetric RNA Duplexes as Next Generation RNAi Inducers," Gene Silencing: Theory, Techniques and Applications, (2010), pp. 343-348.
Li et al., "Inhibition of connective tissue growth factor by siRNA prevents liver fibrosis in rats," The Journal of Gene Medicine, (2006), 8:889-900.
Lima et al., "Human Dicer Binds Short Single-strand and Double-strand RNA with High Affinity and Interacts with Different Regions of the Nucleic Acids" The Journal of Biological Chemistry (2009), 284:2535-2548.
Luo et al., "Inhibition of Connective Tissue Growth Factor by Small Interfering RNA Prevents Renal Fibrosis in Rats Undergoing Chronic Allograft Nephropathy," Transplantation Proceedings, (2008), 40:2365-2369.
Marques et al., "A structural basis for discriminating between self and nonself double-stranded RNAs in mammalian cells," Nature Biotechnology, 24: 559-565 (2006).
Martinez et al., "Singe-Stranded Antisense siRNAs Guide Target RNA Cleavage in RNAi," Cell, 110: 563-574 (2002).
Opalinska et al., "Nucleic-acid Therapeutics: Basic Principles and Recent Applications," Nature Rev, 1 (7): 503-514 (2002).
Paroo et al., "Challenges for RNAi in vivo," Trends in Biotech, 22(8): 390-394 (2004).
Patel et al., "A Novel Protective Role for the Innate Immunity Toll-Like Receptor 3 (TLR3) in the Retina via Stat3," Mol Cell Neurosci, 63: 38-48 (2014).
Raouane et al., "Lipid conjugated oligonucleotides: a useful strategy for delivery," Bioconjugate Chem, 23:1091-104 (2012).
Rose et al., "Functional Polarity is Introduced by Dicer Processing of Short Substrate RNAs," Nucleic Acids Res, 33: 4140-4156 (2005).
Sano et al., "Effect of asymmetric terminal structures of short RNA duplexes on the RNA interference activity and strand selection," Nucleic Acids Research (2008), 36: 5812-5821.
Sharp et al., "RNA-interference-2001," Genes & Development, (2001), 15:485-490.
Sioud et al., "Cationic liposome-mediated delivery of siRNAs in adult mice," Biochem Biophys Res Commun. Dec. 26, 2003; 312(4):1220-5.
Sisco et al., "Antisense Inhibition of Connective Tissue Growth Factor (CTGF/CCN2) mRNA Limits Hypertrophic Scarring Without Affecting Wound Healing in Vivo," Wound Repair Regen, 16: 661-673 (2008).
Song et al., "The Crystal Structure of the Argonaute2 PAZ Domain Reveals an RNA Binding Motif in RNAi Effector Complexes," Nat Struct Biol, 10(12): 1026-1032 (2003).
Soutschek et al., "Therapeutic Silencing of an Endogenous Gene by Systemic Adminstration of Modified siRNAs," Nature, 432: 173-178 (2004).
Sun et al., "Asymmetric RNA duplexes mediate RNA interference in mammalian cells," Nature Biotechnology, 26: 1379-1382 (2008).
Ui-Tei et al., "Essential Notes Regarding the Design of Functional siRNAs for Efficient Mammalian RNAi," J Biomed Biotechnol, 2006; 2006(4):65052. doi: 10.1155/JBB/2006/65052.
Ui-Tei et al., "Guidelines for the selection of highly effective siRNA sequences for mammalian and chick RNA interference," (2004), Nucleic Acids Research, vol. 32, pp. 936-948.
Vasdudevan et al., "Switching from Repression to Activation: MicroRNAs Can Up-Regulate Translation," Science, 318: 1931-1934 (2007).
Wang et al., "Nucleation, Propagation and Cleavage of Target RNAs in Ago Silencing Complexes," Nature, 461: 754-762 (2009).
Yang et al., "HENI recognizes 21-24 nt small RNA duplexes and deposits a methyl group onto the 2' OH of the 3' terminal nucleotide," Nucleic Acids Research, 34: 667-675 (2006).
Yuan et al., "Asymmetric siRNA: New Strategy to Improve Specificity and Reduce Off-Target Gene Expression," Human Gene Therapy 23:521-532 (2013).
Zamore, "RNA interference: listening to the sound of silence," Nature Structural Biology, (2001), 8(9):746-750.
International Search Report & Written Opinion PCT Appl. No. PCT/IB2018/000330, dated Aug. 24, 2018, 12 pages.
Kariko, et al., "Suppression of RNA recognition by Toll-like receptors: the impact of nucleoside modification and the evolutionary origin of RNA," Immunity 23:165-175 (2005).

\* cited by examiner

Figure 1A 19
5'-UUCACCUUGAUGCCAUUCU-3'
3'-AAGUGGAACUACGGUAAGA-5'

38
5'-UUCACCUUGAUGCCAUUCUCCAAUCAUCCAAAAAAUUA-3'
3'-AAGUGGAACUACGGUAAGAGGUUAGUAGGUUUUUUAAU-5'

50
5'-UUCACCUUGAUGCCAUUCUUGGCCUAAGCUCCCAAUCAUCCAAAAAAUUA-3'
3'-AAGUGGAACUACGGUAAGAACCGGAUUCGAGGGUUAGUAGGUUUUUUAAU-5'

60
5'-UUCACCUUGAUGCCAUUCUUGGCCUUGUCGAAAAAAAGCUCCCAAUCAUCCAAAAAAUUA-3'
3'-AAGUGGAACUACGGUAAGAACCGGAACAGCUUUUUUUCGAGGGUUAGUAGGUUUUUUAAU-5'

Figure 1B

19+2
5'-UUCACCUUGAUGCCAUUCUTT-3'
3'-TTAAGUGGAACUACGGUAAGA-5'

38+2
5'-UUCACCUUGAUGCCAUUCUCCAAUCAUCCAAAAAAUUATT-3'
3'-TTAAGUGGAACUACGGUAAGAGGUUAGUAGGUUUUUUAAU-5'

50+2
5'-UUCACCUUGAUGCCAUUCUUGGCCUAAGCUCCCAAUCAUCCAAAAAAUUATT-3'
3'-TTAAGUGGAACUACGGUAAGAACCGGAUUCGAGGGUUAGUAGGUUUUUUAAU-5'

60+2
5'-UUCACCUUGAUGCCAUUCUUGGCCUUGUCGAAAAAAAGCUCCCAAUCAUCCAAAAAAUUATT-3'
3'-TTAAGUGGAACUACGGUAAGAACCGGAACAGCUUUUUUUCGAGGGUUAGUAGGUUUUUUAAU-5'

Figure 1C

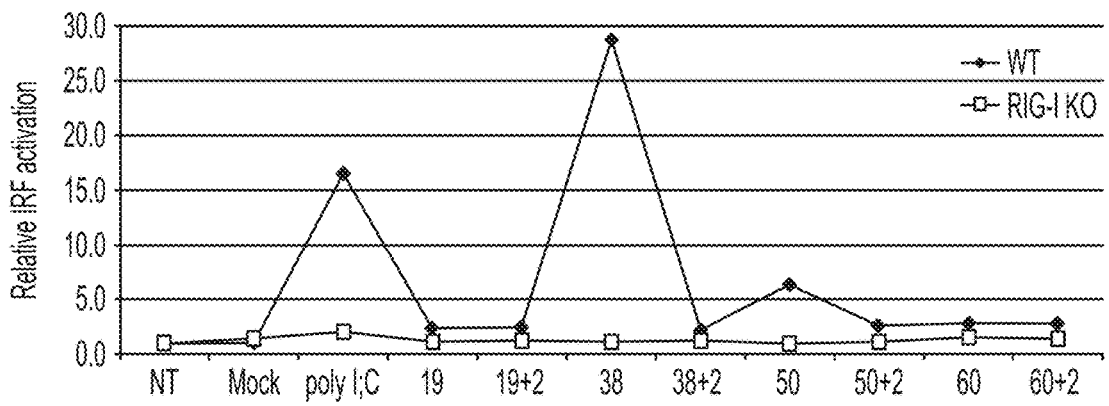

Figure 5A

| | Length | Sequences | SEQ ID NO: |
|---|---|---|---|
| survivin targeting dsRNA | 40(+2) | 5' UGA AAA UGU CCU UUC CUA AGA CAU UGC UAA GGG G (CC)<br>3' (AA) ACU UUU ACA ACU AGA GGA AAG GAU UCU GUA ACG AUU CCC C | SEQ ID NO:27<br>SEQ ID NO:28 |
| | 50(+2) | 5' UGA AAA UGU UGA UCU CCU UUC CUA AGA CAU UGC UAA GGG GCC CAC AGG AA (GG)<br>3' (AA) ACU UUU ACA ACU AGA GGA AAG GAU UCU GUA ACG AUU CCC CGG GUG UCC UU | SEQ ID NO:29<br>SEQ ID NO:30 |
| | 60(+2) | 5' UGA AAA UGU UGA UCU CCU UUC CUA AGA CAU UGC UAA GGG GCC CAC AGG AAG GCU GGC (AC)<br>3' (AA) ACU UUU ACA ACU AGA GGA AAG GAU UCU GUA ACG AUU CCC CGG GUG UCC UUC CGA CCA CCG | SEQ ID NO:31<br>SEQ ID NO:32 |

Figure 6A

| | name | sequence | |
|---|---|---|---|
| luciferase-GFP targeting dsRNA | 38 Antisense | 5' UUCACCCUUGAUGCCAAUCCAAUCAUCCAAAAAAUUA | SEQ ID NO: 3 |
| | 38 Sense | 3' AAGUGGAACUACGGUAAGAGAGGUUAGGUUUUUAAU | SEQ ID NO: 4 |
| | 50 Antisense | 5' UUCACCCUUGAUGCCAAUCCUAAGCUCCAAUCAUCCAAAAAAUUA | SEQ ID NO: 5 |
| | 50 Sense | 3' AAGUGGAACUACGGUAAGAGAUUCGAGGUAGUAGGUUUUUAAU | SEQ ID NO: 6 |
| | 60 Antisense | 5' UUCACCCUUGAUGCCAAUCCUUGGCCUUGUCGAAACCCGAAUCAUCCAAAAAAUUA | SEQ ID NO: 7 |
| | 60 Sense | 3' AAGUGGAACUACGGUAAGAGAACCGGAACAGCUUUGGGCUUAGUAGGUUUUUAAU | SEQ ID NO: 8 |
| | 38+2 Antisense | 5' UUCACCCUUGAUGCCAAUCCAAUCAUCCAAAAAAUUAdTdT | SEQ ID NO: 11 |
| | 38+2 Sense | 3' dTdTAAGUGGAACUACGGUUAAGAGAGGUUAGGUUAGUAGGUUUUUAAU | SEQ ID NO: 12 |
| | 50+2 Antisense | 5' UUCACCCUUGAUGCCAAUCCGAUUCGGUAAGAACGGAAUCAUCCAAAAAAUUAdTdT | SEQ ID NO: 13 |
| | 50+2 Sense | 3' dTdTAAGUGGAACUACGGUAAGAGAUUCGAGGUAGUAGGUUUUUAAU | SEQ ID NO: 14 |
| | 60+2 Antisense | 5' UUCACCCUUGAUGCCAAUCCUUGGCCUUGUCGAAACCCGAAUCAUCCAAAAAAUUAdTdT | SEQ ID NO: 15 |
| | 60+2 Sense | 3' dTdTAAGUGGAACUACGGUAAGAGAACCGGAACAGCUUUGGGCUUAGUAGGUUUUUAAU | SEQ ID NO: 16 |

Figure 6B

| | name | sequence | |
|---|---|---|---|
| survivin targeting dsRNA | 30 Antisense | 5' UGAAAAUGUUGAUCUCCUUUCCUAAGACAU | SEQ ID NO: 17 |
| | 30 Sense | 3' ACUUUUACAACUAGAGGAAAGGAUUCUGUA | SEQ ID NO: 18 |
| | 40 Antisense | 5' UGAAAAUGUUGAUCUCCUUUCCUAAGACAUUGCUAAGGGG | SEQ ID NO: 19 |
| | 40 Sense | 3' ACUUUUACAACUAGAGGAAAGGAUUCUGUAACGAUUCCCC | SEQ ID NO: 20 |
| | 50 Antisense | 5' UGAAAAUGUUGAUCUCCUUUCCUAAGACAUUGCUAAGGGGCCCACAGGAA | SEQ ID NO: 21 |
| | 50 Sense | 3' ACUUUUACAACUAGAGGAAAGGAUUCUGUAACGAUUCCCCGGGUGUCCUU | SEQ ID NO: 22 |
| | 60 Antisense | 5' UGAAAAUGUUGAUCUCCUUUCCUAAGACAUUGCUAAGGGGCCCACAGGAAGGCUGGUGGC | SEQ ID NO: 23 |
| | 60 Sense | 3' ACUUUUACAACUAGAGGAAAGGAUUCUGUAACGAUUCCCCGGGUGUCCUUCCGACCACCG | SEQ ID NO: 24 |
| | 30+2 Antisense | 5' UGAAAAUGUUGAUCUCCUUUCCUAAGACAUUG | SEQ ID NO: 25 |
| | 30+2 Sense | 3' AAACUUUUACAACUAGAGGAAAGGAUUCUGUA | SEQ ID NO: 26 |
| | 40+2 Antisense | 5' UGAAAAUGUUGAUCUCCUUUCCUAAGACAUUGCUAAGGGGCC | SEQ ID NO: 27 |
| | 40+2 Sense | 3' AAACUUUUACAACUAGAGGAAAGGAUUCUGUAACGAUCCCC | SEQ ID NO: 28 |
| | 50+2 Antisense | 5' UGAAAAUGUUGAUCUCCUUUCCUAAGACAUUGCUAAGGGGCCCACAGGAAGG | SEQ ID NO: 29 |
| | 50+2 Sense | 3' AAACUUUUACAACUAGAGGAAAGGAUUCUGUAACGAUUCCCCGGGUGUCCUU | SEQ ID NO: 30 |
| | 60+2 Antisense | 5' UGAAAAUGUUGAUCUCCUUUCCUAAGACAUUGCUAAGGGGCCCACAGGAAGGCUGGUGGCAC | SEQ ID NO: 31 |
| | 60+2 Sense | 3' AAACUUUUACAACUAGAGGAAAGGAUUCUGUAACGAUUCCCCGGGUGUCCUUCCGACCACCG | SEQ ID NO: 32 |
| | si-survivin Antisense | 5' UCACACAAGUCAUGCAUdTdT | SEQ ID NO: 33 |
| | si-survivin Sense | 3' dTdTAGUGUGUUCAGUACGUA | SEQ ID NO: 34 |

SEQUENCE LISTING

```
<160> NUMBER OF SEQ ID NOS: 34

<210> SEQ ID NO 1
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 1
uucaccuuga ugccauucu                                                       19

<210> SEQ ID NO 2
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 2
aaguggaacu acgguaaga                                                       19

<210> SEQ ID NO 3
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 3
uucaccuuga ugccauucuc caaucaucca aaaaauua                                  38

<210> SEQ ID NO 4
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 4
aaguggaacu acgguaagag guuaguaggu uuuuuaau                                  38

<210> SEQ ID NO 5
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 5
uucaccuuga ugccauucuu ggccuaagcu cccaaucauc caaaaaauua                     50

<210> SEQ ID NO 6
<211> LENGTH: 50
<212> TYPE: DNA
<213> ORGANISM: Artificial Sequence
<220> FEATURE:
<223> OTHER INFORMATION: Synthetic Polynucleotide
```

<400> SEQUENCE: 6 aauggaacu acguaagaa ccggauucga ggguuaguag guuuuuaau          50

<210> SEQ ID NO 7
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 7
uucaccuuga ugccauucuu ggccuugucg aaaaaaagcu cccaaucauc caaaaauua   60

<210> SEQ ID NO 8
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 8 aauggaacu acguaagaa ccggaacagc uuuuuucga ggguuaguag guuuuuaau    60

<210> SEQ ID NO 9
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 9
uucaccuuga ugccauucut t                                      21

<210> SEQ ID NO 10
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 10
ttaaguggaa cuacgguaag a                                      21

<210> SEQ ID NO 11
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 11
uucaccuuga ugccauucuc caaucaucca aaaauuatt                   40

<210> SEQ ID NO 12
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 12
ttaaguggaa cuacgguaag agguuaguag guuuuuaau                   40

```
<210> SEQ ID NO 13
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 13
uucaccuuga ugccauucuu ggccuaagcu cccaaucauc caaaaaauua tt         52

<210> SEQ ID NO 14
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 14
ttaaguggaa cuacgguaag aaccggauuc gaggguuagu agguuuuuua au         52

<210> SEQ ID NO 15
<211> LENGTH: 62
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(32)
<223> OTHER INFORMATION: n is a, c, g, t or u

<400> SEQUENCE: 15
uucaccuuga ugccauucuu ggccuugucg anaaaaagcu cccaaucauc caaaaaauua         60
tt                                                                        62

<210> SEQ ID NO 16
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 16
uucaccuuga ugccauucuu ggccuugucg aaaaaaagcu cccaaucauc caaaaaauua         60
tt                                                                        62

<210> SEQ ID NO 17
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 17
ugaaaauguu gaucuccuuu ccuaagacau                                  30

<210> SEQ ID NO 18
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 18
acuuuuacaa cuagaggaaa ggauucugua                                  30
```

```
<210> SEQ ID NO 19
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 19
ugaaaauguu gaucuccuuu ccuaagacau ugcuaagggg                              40

<210> SEQ ID NO 20
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 20
acuuuuacaa cuagaggaaa ggauucugua acgauccccc                              40

<210> SEQ ID NO 21
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 21
ugaaaauguu gaucuccuuu ccuaagacau ugcuaagggg cccacaggaa                   50

<210> SEQ ID NO 22
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 22
acuuuuacaa cuagaggaaa ggauucugua acgauccccc ggguguccuu                   50

<210> SEQ ID NO 23
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 23
ugaaaauguu gaucuccuuu ccuaagacau ugcuaagggg cccacaggaa ggcuggguggc       60

<210> SEQ ID NO 24
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 24
acuuuuacaa cuagaggaaa ggauucugua acgauccccc ggguguccuu ccgaccaccg       60

<210> SEQ ID NO 25
<211> LENGTH: 32
<212> TYPE: DNA
<213> ORGANISM: Artificial Sequence
<220> FEATURE:
<223> OTHER INFORMATION: Synthetic Polynucleotide
```

```
<400> SEQUENCE: 25
ugaaaauguu gaucuccuuu ccuaagacau ug                              32

<210> SEQ ID NO 26
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 26
aaacuuuuac aacuagagga aaggauucug ua                              32

<210> SEQ ID NO 27
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 27
ugaaaauguu gaucuccuuu ccuaagacau ugcuaagggg cc                   42

<210> SEQ ID NO 28
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 28
aaacuuuuac aacuagagga aaggauucug uaacgauucc cc                   42

<210> SEQ ID NO 29
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 29
ugaaaauguu gaucuccuuu ccuaagacau ugcuaagggg cccacaggaa gg        52

<210> SEQ ID NO 30
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 30
aaacuuuuac aacuagagga aaggauucug uaacgauucc ccgggugucc uu        52

<210> SEQ ID NO 31
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 31
ugaaaauguu gaucuccuuu ccuaagacau ugcuaagggg cccacaggaa ggcugguggc    60
ac                                                                   62
```

```
<210> SEQ ID NO 32
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 32
aaacuuuuac aacuagagga aaggauucug uaacgauucc ccggguqucc uuccgaccac    60 cg                                                                  62

<210> SEQ ID NO 33
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 33
ucacacacaa gucaugcaut t                                             21

<210> SEQ ID NO 34
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 34
ttagugugug uucaguacgu a                                             21
```

LONG DOUBLE-STRANDED RNA FOR RNA INTERFERENCE

CROSS-REFERENCE TO RELATED APPLICATIONS

This application is a 371 national phase filing of international application PCT/IB2018/000330, filed Feb. 12, 2018, which claims the benefit of and priority to U.S. Provisional Patent Application No. 62/457,282 filed Feb. 10, 2017, the content of which is hereby incorporated by reference in its entirety.

FIELD

The present technology relates, in part, to long double stranded RNA useful in inhibiting gene expression.

SEQUENCE LISTING

The instant application contains a Sequence Listing which has been submitted in ASCII format via EFS-Web and is hereby incorporated by reference in its entirety. Said ASCII copy, created on Feb. 12, 2018, is named OLX-003PC_Sequence Listing_ST25.txt and is 8,192 bytes in size.

BACKGROUND

RNA interference (RNAi) is an evolutionarily conserved biological process in which a double-stranded RNA (dsRNA) inhibits gene expression by neutralizing a targeted messenger RNA (mRNA) having a complementary nucleotide sequence (Hannon et al., Nature, 418:244-251, 2002). The RNAi pathway is initiated by the Dicer endonuclease, which cleaves long dsRNAs into short interfering RNA (siRNA) fragments having 19 complementary base-paired nucleotides and a 3' overhang of two nucleotides at each end. siRNAs are unwound into two single-stranded RNAs, a passenger strand and a guide strand. The guide strand is incorporated into an RNA-induced silencing complex (RISC). Post-transcriptional gene silencing occurs when an antisense sequence in the guide strand pairs with a complementary sequence in a mRNA and induces cleavage by Argonaute 2 (Ago2), the catalytic component of the RISC complex.

RNAi was first discovered in nematodes and arthropods (Fire et al., Nature, 391:806-811, 1998). In these phyla, RNAi can be induced with dsRNAs of 0.3 to 1 kb. This RNAi procedure failed in mammalian cells due to activation of an immune response (Stark et al., Annu. Rev. Biochem., 67:227-264, 1998). This form of innate immunity, manifested by the induction of interferon expression, is mediated by pattern recognition receptors that bind to a form of RNA typically associated with viral infections. To avoid activating an antiviral response, RNAi in mammalian cells is often induced using synthetic 21-mer siRNAs that mimic the digestion products of dicer (Elbashir et al., Nature, 411:494-498, 2001).

RNA duplexes of 25-30 nucleotides in length can be up to 100-fold more potent than corresponding conventional 21-mer siRNAs. The enhanced potency of these 25-30 bp duplexes is attributed to the fact that they are Dicer substrates, directly linking the production of siRNAs to incorporation into the RISC complex (Kim et al., Nat. Biotechnol. 23:222-6, 2005). Even longer dsRNA duplexes can inhibit the expression of two different target mRNA sequences. Simultaneous downregulation of two mRNAs with a single dsRNA construct was most efficient when the 5' ends of the antisense sequences were located at either end of the dsRNA (Chang et al., Mol. Cells 27, 689-695, 2009).

Increasing the length of a blunt-ended dsRNA to 27 bp induced interferon expression in the immune-sensitive T98G cell line (Marques et al., Nat. Biotechnol. 24:559-65, 2006). Observations like this discouraged the development of longer interfering RNAs.

Efficient gene silencing constructs with minimal activation of the innate immune response are needed, including constructs that can selectively target more than one mRNA or more than one mRNA region. The invention meets this and other objectives.

BRIEF DESCRIPTION OF THE DRAWING

FIG. 1A is the complementary nucleotide sequences of the two strands of various blunt-ended dsRNAs differing in length (i.e., blunt-ended dsRNAs with lengths of 19 bp (top strand is SEQ ID NO: 1; bottom strand is SEQ ID NO: 2), 38 bp (top strand is SEQ ID NO: 3; bottom strand is SEQ ID NO: 4), 50 bp (top strand is SEQ ID NO: 5; bottom strand is SEQ ID NO: 6), and 60 bp (top strand is SEQ ID NO: 7; bottom strand is SEQ ID NO: 8).

FIG. 1B is the complementary nucleotide sequences of the two strands of various dsRNAs with 2 bp 3' overhangs that differ in their length (i.e., dsRNAs with lengths of 19+2 (top strand is SEQ ID NO: 9; bottom strand is SEQ ID NO: 10), 38+2 (top strand is SEQ ID NO: 11; bottom strand is SEQ ID NO: 12), 50+2 (top strand is SEQ ID NO: 13; bottom strand is SEQ ID NO: 14), and 60+2 (top strand is SEQ ID NO: 15; bottom strand is SEQ ID NO: 16).

FIG. 1C is a graph showing antiviral responses activated by the indicated dsRNAs in wild type RAW 264.7 cells and RAW 264.7 RIG-I knockout cells.

FIG. 5A is a table showing the nucleotide sequences for the 40+2, 50+2, and 60+2 survivin targeting dsRNA.

FIG. 6A is a table showing the nucleotide sequences for the luciferase-GFP targeting dsRNA of Example 1.

FIG. 6B is a table showing the nucleotide sequences for survivin targeting dsRNA of Example 2 (i.e., 30 bp, 30+2, 40 bp, 40+2, 50 bp, 50+2, 60 bp, and 60+2). FIG. 6B also shows the nucleotide sequences for conventional survivin siRNA (si-survivin; si-sur 19+2).

DESCRIPTION OF THE INVENTION

Figure 2:
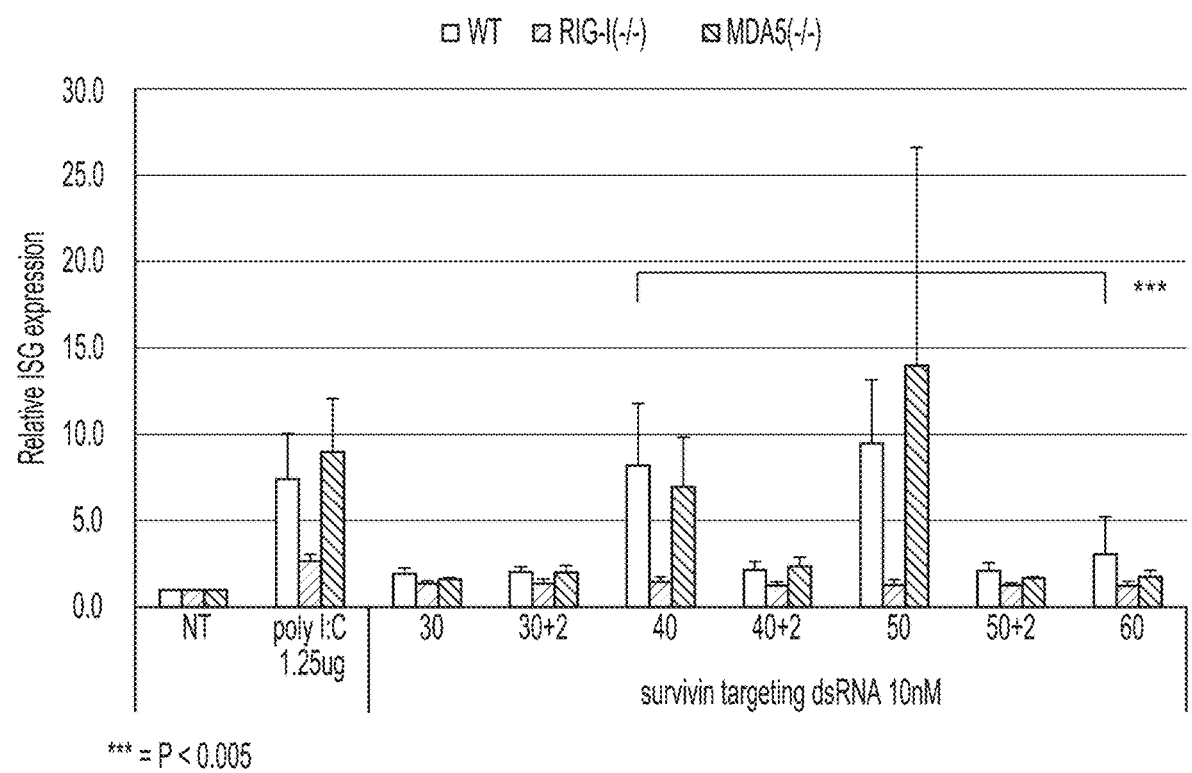
FIG. 2 is a graph showing the relative ISG expression by blunt-ended dsRNAs targeting the survivin gene with lengths of 30, 40, 50, and 60 base pairs and the relative ISG expression of the dsRNAs targeting the survivin gene having a two nucleotide 3' overhang in wild type RAW 264.7 cells, RAW 264.7 RIG-I knockout cells, and RAW 264.7 MDAS knockout cells.

The present invention provides long double-stranded RNAs (ldRNAs) that can inhibit gene expression in mammalian cells without inducing significant antiviral response, and methods for gene silencing using the same. Surprisingly, although a blunt 38-mer dsRNA has been shown to strongly induce interferon expression, this cellular response was not observed when the length of the blunt dsRNA was increased, including to constructs having 50 or 60 base pairs, and optionally one or more 3' dinucleotide overhangs. These longer constructs can be efficient gene silencers, and may provide the ability to silence a plurality of mRNAs or mRNA regions.

In accordance with embodiments, each end of an ldRNA can be blunt, or it can have a 3' overhang. Some ldRNAs are blunt on both ends. The siRNA products of dicer cleavage events have a 3' overhang of two nucleotides on both ends. These 3' overhangs inhibit recognition RIG-I, a pattern recognition receptor with RNA helicase activity (Marques et al., Nat. Biotechnol. 24:559-65, 2006). In contrast, some viruses produce dsRNAs with blunt ends. These foreign dsRNAs can induce the expression of interferon and other genes characteristic of innate immunity. However, various ldRNAs according to embodiments of the present invention cause little or no activation of an antiviral response.

Various ldRNAs of the present invention comprise a duplex that is at least 40 bp, or at least 45 bp, or at least 50 bp, or at least 60 bp, or at least 80 bp, or at least 100 bp in length. In various embodiments, the ldRNA comprises a duplex that is no more than 200 bp, or no more than 150 bp, or no more than 100 bp in length. For example, various ldRNAs according to embodiments of the invention comprise a duplex that is from 40 to 200 bp in length, or from 40 to 150 bp in length, or from 40 to 100 bp in length; or from 50 to 200 bp in length, or from 50 to 150 bp in length, or from 50 to 100 bp in length. In some embodiments, the ldRNA comprises a duplex that is 40 to 80 bp in length, 45 to 80 bp in length, 50 to 80 bp in length, 40 to 60 bp in length, 45 to 60 bp in length, or 50-60 bp in length.

In various embodiments, the duplex comprises two RNA strands that are substantially complementary. In some embodiments, the duplex contains only canonical base pairing, with complete complementarity. In some embodiments, the RNA comprises up to 10, or up to 5 (e.g., 1, 2, or 3) mismatched bases or non-canonical base pairs (e.g., G:U base pairs).

In some embodiments, both ends of the ldRNA are blunt. In some embodiments, one or both ends comprise an overhang on a 3' end. In some embodiments, the overhang is a dinucleotide overhang (e.g., dTdT).

Induction of an antiviral (innate immune) response is determined by measuring relative interferon activation. Various ldRNAs of the present invention induce interferon or IRF expression to not more than 15, not more than 10, or not more than 5 times the expression level induced by a mock transfection in cell lines, which include, but are not limited to, wild type RAW 264.7 cells, RAW 264.7 RIG-I knockout cells, and RAW 264.7 MDAS knockout cells.

Various ldRNAs of the present invention can reduce the expression of a target gene via the RNAi pathway. These ldRNAs comprise a guide sequence of at least 8 bp that is complementary to a target mRNA. In some embodiments, the ldRNA comprises 2, 3, 4, or more guide sequences complementary to different segments within a single mRNA. In other embodiments, the ldRNA of the present invention has guide sequences complementary to 2, 3, 4, or more different target mRNAs. In some embodiments, the sequences complementary to an mRNA are independently selected from sequences that are in the range of 8 to 50 nucleotides, or in the range of 8 to 40 nucleotides, or in the range of 8 to 30 nucleotides, or in the range of 8 to 20 nucleotides. In some embodiments, the sequences complementary to an mRNA are independently selected from sequences that are in the range of 15 to 50 nucleotides, or in the range of 15 to 40 nucleotides, or in the range of 15 to 30 nucleotides, or in the range of 15 to 20 nucleotides. For example, the complementary sequences may be about 15 nt, about 16 nt, about 17 nt, about 18 nt, about 19 nt, or about 20 nt.

The guide sequences in an ldRNA are antisense sequences. They can bind to an mRNA in the 5' untranslated region, start site, coding sequence, stop site, or 3' untranslated region. Preferentially, they bind to an accessible segment within the targeted mRNA.

ldRNAs are dsRNAs wherein the two strands are complementary to each other and oriented in opposite directions. Thus, the 5' end of one RNA strand and the 3' end of the other RNA strand are located at the same end of the ldRNA. Some ldRNAs comprise a guide sequence wherein the 5' end of the guide sequence is located at the 5' end of one RNA strand of the ldRNA. Other ldRNAs comprise two guide sequences wherein the 5' ends of the two guide sequences are located at the 5' ends of the two RNA strands, which are themselves located at opposite ends of the ldRNA.

The RNAi activity of an ldRNA can be determined by measuring levels of the target mRNA using conventional methods such as Northern blotting, quantitative rtPCR, and other techniques well-known in the art. Target mRNA levels will be reduced if the ldRNA has RNAi activity. If the RNAi activity of an ldRNA is specific for the targeted mRNA, the levels of non-targeted mRNAs will not be reduced. Alternatively, RNAi activity can be indirectly measured by quantitating the expression or activity of a protein encoded by the targeted mRNA. Protein expression and activity are determined by conventional methods known in the art, such as enzyme linked immunosorbant assays (ELISAs) and enzyme assays.

The RNA strands in an ldRNA can have a modified backbone, modified nucleotides, and/or other chemical modifications.

The phosphate backbone of one or both RNA strands in an ldRNA can be substituted with one or more phosphorothioate linkages. The canonical RNA backbone found in nature includes phosphodiester linkages between nucleotides. The phosphorothioate bond modification alters the phosphate linkage by replacing one of the non-bridging oxygens with a sulfur atom. This alteration changes the overall chemical properties of the polynucleotide. In particular, adding phosphorothioate bonds can stabilize the polynucleotide backbone against nuclease degradation, effectively increasing its half-life in a cellular milieu. Phosphorothioate linkages can be incorporated into either or both strands of an ldRNA. In some embodiments, at least about 1%, 2%, 4%, 8%, 16%, 32% or about 50% of the nucleotides of an ldRNA are linked by phosphorothioate bonds.

An ldRNA can be synthesized from non-canonical nucleotides such as, but not limited to, pseudouridine, N1-methylpseudouridine and/or 5-methylcytidine. Such nucleotides can reduce the activation of innate immunity via toll-like receptors.

An ldRNA can be designed to target almost any mRNA. For example, various ldRNAs reduce the level of mRNAs encoding enzymes, transcription factors, signaling proteins, kinases, phosphatases, ion channels, cytoplasmic proteins, membrane proteins, and secreted proteins.

An ldRNA can target a viral mRNA. In some embodiments, multiple guide sequences in an ldRNA are complementary to different segments of a single target viral mRNA.

In other embodiments, guide sequences within a single ldRNA are complementary to sequences in two or more viral mRNA targets.

Various ldRNAs target mRNAs that encode proteins implicated in pathways critical for cancer cell growth and/or survival. Reducing expression of such proteins reduces the growth or survival of cancerous cells. In various embodiments, ldRNAs of the present invention comprise two or more guide sequences for proteins implicated in pathways critical for cancer cell growth and/or survival. The present invention also provides methods of treating a cancer patient with an ldRNA that lowers the levels of an mRNA implicated in cancer.

Various ldRNAs target mRNAs that encode signal transduction proteins. An ldRNA can target two or more different segments of an mRNA encoding a signal transduction protein. Alternatively, guide sequences within a single multifunctional ldRNA can target two or more mRNAs encoding related signal transduction proteins. Related signal transduction proteins may function in the same signal transduction pathway, in parallel signal transduction pathways, or in signal transduction pathways that diverge from a common origin. A multifunctional ldRNA may also target mRNAs encoding proteins that act in independent signal transduction pathways.

The present invention includes methods for reducing the expression of a target gene by administering an ldRNA of the present invention to cells, tissues or animals. A subject can be a human or animal subject or patient in need of treatment for a disease or condition, or at risk of a disease or condition. The composition can be administered to cells ex vivo or in vivo.

Any mammalian cell is suitable for ldRNA treatment regardless of whether it is sensitive or insensitive to the induction of innate immunity by dsDNA. For example, ldRNA can be administered to immune-sensitive T98G glioblastoma cells and immune-insensitive HeLa carcinoma cells. Expression of a target gene can be inhibited in both cell types, and interferon expression will be lower after ldRNA administration than it would have been after administration of a blunt-ended 38 bp dsRNA. Non-limiting examples of cell types that can be induced to express proteins by contact with ldRNA include keratinocytes, melanocytes, macrophage, hepatocytes, pneumocytes, fibroblasts, smooth muscle cells, and lymphocytes (e.g., B cell or T cell, or precursor cell thereof). Furthermore, an ldRNA can induce protein expression by hyperplastic cells, malignant cells and stem cells. In various embodiments, the target cell is selected from an antigen-presenting cell, a dendritic cell, a macrophage, a neural cell, a spleen cell, a lymphoid cell, a lung cell (e.g., an alveolar cell), a skin cell (e.g., a keratinocyte or fibroblast), an endothelial cell, an astrocyte, a microglial cell, a mesenchymal cell, an epithelial cell, or a hematopoietic cell.

An ldRNA can be administered to various tissues including skin, retina, lungs, liver, heart, and the like. Additionally, an ldRNA can be systemically administered to a whole animal. Systemic administration is expected to lead to uptake by both immune-sensitive and immune resistant cells. An ldRNA can be safely administered to a mixed population of cells including immune-sensitive cells because it is less immunogenic than other dsRNAs.

In various embodiments, an ldRNA of the present invention may be incorporated into a pharmaceutical formulation. Non-limiting examples of pharmaceutical formulations include a topical cream or ointment or an aqueous or buffered solution optionally comprising a stabilizing agent. A pharmaceutical formulation may further comprise a vehicle to facilitate cellular uptake by cells and tissues.

Pharmaceutically acceptable carriers or diluents are well known to those skilled in the art. The carrier or diluent may be may be, in various embodiments, a solid carrier or diluent for solid formulations, a liquid carrier or diluent for liquid formulations, or mixtures thereof.

In another embodiment, solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In some embodiment, the pharmaceutical compositions are controlled-release compositions, i.e. compositions in which the ldRNA is released over a period of time after administration. Controlled- or sustained-release compositions include formulation in lipophilic depots (e.g. fatty acids, waxes, oils). In another embodiment, the composition is an immediate-release composition, i.e. a composition in which the entire compound is released immediately after administration.

An ldRNA is, in another embodiment, formulated into the composition as neutralized pharmaceutically acceptable salt form.

Persons of ordinary skill will understand that the mode of administering an ldRNA to a subject will depend upon the targeted mRNA, the target cell, the disease or condition to be treated, and the form of the pharmaceutical formulation.

An ldRNA can be administered by various methods known in the art. For example, an ldRNA can be administered by inhalation, intravenous injection, or topically. In some embodiments, the ldRNA is administered to patients in an effective amount, for example, by subcutaneous injection, intradermal injection, intramuscular injection, intraocular injection, or intratumoral injection, or other forms of parenteral administration.

In some embodiments, ldRNAs are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the ldRNA is formulated in a capsule. In accordance with this embodiment, the compositions of the present invention comprise, in addition to the active compound and the inert carrier or diluent, a hard gelatin capsule.

In another embodiment, the ldRNA is administered topically to body surfaces and are thus formulated in a form suitable for topical administration. Suitable topical formulations include gels, ointments, creams, lotions, drops and the like. For topical administration, the compositions or their physiologically tolerated derivatives are prepared and applied as solutions, suspensions, or emulsions in a physiologically acceptable diluent with or without a pharmaceutical carrier.

In another embodiment, the ldRNA is administered as a suppository, for example a rectal suppository or a urethral suppository. In another embodiment, the pharmaceutical composition is administered by subcutaneous implantation of a pellet. In another embodiment, the pellet provides for controlled release of agent over a period of time.

In various embodiments, the dosage is a daily dose, a weekly dose, a monthly dose, or an annual dose. In some embodiments, the dose is a one-time dose, or the composition is administered at least 10 times. In some embodiments, the composition is administered at least 6 or at least 12 times per year, for a plurality of years.

The present invention provides methods for the treatment of various diseases or conditions by administering an ldRNA. The ldRNA will reduce the expression of one or more deleterious target genes, thereby treating the disease or condition. For example, diseases or conditions affecting the skin can be treated with an ldRNA. Skin diseases or conditions suitable for treatment with an ldRNA include skin whitening, darkening, or scarring, atopic dermatitis, psoriasis, scleroderma, hair loss or wrinkled skin. An ldRNA can also be administered for the treatment of a disease or condition manifest by fibrosis. Fibrotic diseases or conditions that may be treated with an ldRNA are liver fibrosis, retinal fibrosis, and pulmonary fibrosis (e.g., idiopathic pulmonary fibrosis). Ocular conditions that can be treated with an ldRNA include macular degeneration (wet or dry AMD). Inflammatory conditions that can be treated with an ldRNA include rheumatoid arthritis and Crohn's disease. In some embodiments, the condition is neuropathic pain. In some embodiments, the condition is hypercholesterolemia, atherosclerosis, or heart disease.

In some embodiments, the ldRNA targets a plurality of mRNAs. Exemplary targets include CTGF-encoding mRNA and MYD88 encoding mRNA.

ldRNAs are negatively charged nucleic acid polymers. To facilitate cellular uptake, an ldRNA can be formulated with a vehicle that transports nucleic acids into cells. Suitable vehicles include calcium phosphate, cationic lipids, cationic polymers, polyethyleneimine, and protein-based transfection reagents.

In some embodiments, the transfection reagent forms a liposome. Liposomes can increase intracellular stability, increase uptake efficiency and improve biological activity. Liposomes are hollow spherical vesicles composed of lipids arranged in a similar fashion as those lipids which make up the cell membrane. They may have an internal aqueous space for entrapping water soluble compounds and range in size from 0.2 microns to several microns in diameter. See Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327).

A lipophilic moiety can be conjugated to one or more nucleotides in an ldRNA. Preferentially, the lipophilic moiety is conjugated to the 5' end of one of the RNA strands of an ldRNA. Non-limiting examples of lipophilic moieties include cholesterol, tocopherol, and a long-chain fatty acid having 10 or more carbon atoms such as stearic acid or palmitic acid. A covalently bound lipophilic moiety can facilitate entry of an ldRNA into cells. Such methods are known and described in, for example, PCT/KR2013/004463 and US 2015/0111948, which are incorporated herein by reference in their entireties.

Unless otherwise defined, all technical and scientific terms used herein have the same meaning as commonly understood by one of ordinary skill in the art to which the invention pertains. Generally, the nomenclature used herein are well known and commonly used in the art.

EXAMPLES

Example 1: Immune Responses to Various dsRNAs

To measure immune responses, RAW 264.7 cells were propagated in Dulbecco's Modified Eagle's Media (Gibco) supplemented with 10% fetal bovine serum, 100 µg/ml Normocin (InvivoGen), and 200 µg/ml Zeocin (InvivoGen). Cells were seeded in a 96-well plate at a density of $1.0 \times 10^4$ cells/cm$^2$, and cultured for 24 hours without antibiotics. Cells were transfected with 10 nM dsRNA using RNAiMAX transfection agent (Thermo Fisher Scientific). 24 hours and 48 hours after transfection, 10 µl aliquots of supernatant were sampled into 96-well white plates. 50 µl of Quanti-Luc luciferase substrate (InvivoGen) was added to each well, and plates were read immediately for luciferase activity using a microplate reader (PerkinElmer).

Blunt-ended dsRNAs were synthesized with lengths of 19, 38, 50 and 60 base pairs (FIGS. 1A and 6A). The antiviral response to these dsRNAs was determined by measuring Relative IRF activation (FIG. 1C). As expected the 38 bp dsRNA induced a strong antiviral response and the short, 19 bp dsRNA did not. Surprisingly, the antiviral response to the 50 bp dsRNA was reduced by >80% compared to the response to the 38-mer, and an even lower response was observed for the 60-mer. All of these antiviral responses were substantially eliminated in RIG-I knockout cells, confirming that RIG-I is the dsRNA sensor that recognizes blunt dsRNAs. Additional tests show an antiviral response to the positive control polyIC and no response in mock treated cells. Furthermore, addition of a 2 nucleotide 3' overhang to the dsRNA (FIGS. 1B and 6A) also eliminated the antiviral response, consistent with previous work showing that RIG-1 is not activated by dsRNAs having a 3' overhang (Marques et al., Nat. Biotechnol. 24:559-65, 2006).

Example 2: Immune Responses and Knockdown Efficacy of Long dsRNAs

Figure 5B:
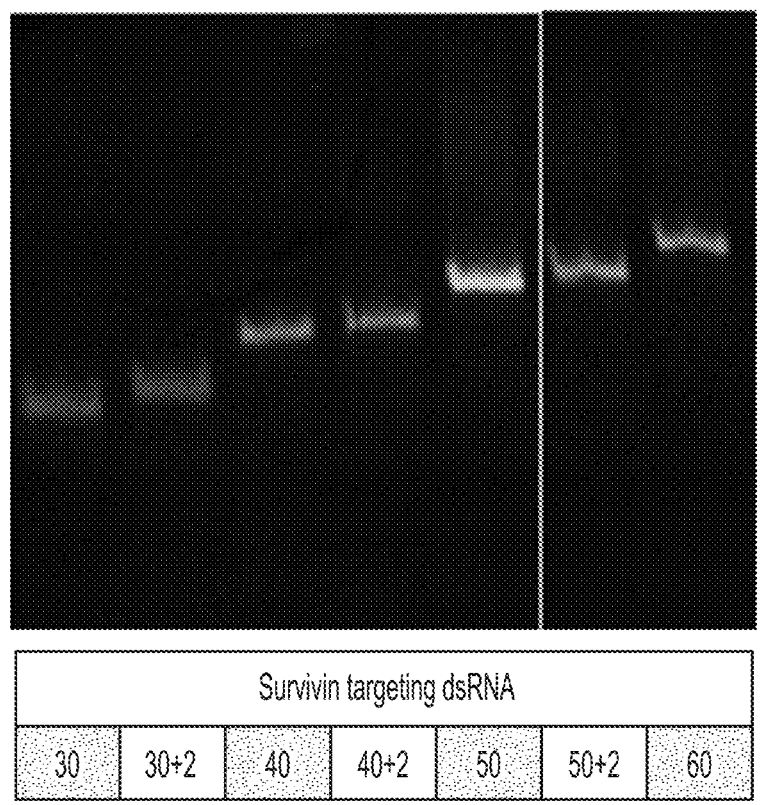
FIG. 5B is an image showing gel bands for the 30 bp, 30+2, 40 bp, 40+2, 50 bp, 50+2, and 60 bp survivin targeting dsRNA.

Blunt-ended dsRNAs targeting the survivin gene were synthesized with lengths of 30, 40, 50 and 60 base pairs (see FIG. 6B). Two nucleotide 3' overhang dsRNAs were also synthesized (i.e., 30+2; 40+2; 50+2; and 60+2). See FIGS. 5A and 6B. The identification of the above disclosed survivin targeting dsRNAs is shown in FIG. 5B. The antiviral response to these dsRNAs was determined by measuring Relative ISG Expression (FIG. 2). The dsRNAs were tested in RAW 264.7 cells that were wild type (WT), RIG-I negative (RIG-I (−/−)), or MDAS negative (MDAS (−/−)).

The results show that some immune stimulation (as measured by relative ISG expression) occurred with 40 bp and 50 bp dsRNA. FIG. 2. However, against conventional concepts, 40 bp and 50 bp dsRNA expressed much more relative ISG as compared to the relative ISG generated by 60 bp dsRNA. FIG. 2.

The 40+2, 50+2, and 60 bp ldRNAs showed very little ISG expression. FIG. 2. The data shows that two nucleotide RNA overhangs at 3' ends (e.g., 40+2 and 50+2) efficiently circumvent innate immune system. FIG. 2.

The results also show that RIG-I deficient cells (RIG-I (−/−)) did not induce the expression of ISG proteins, which indicates that RIG-I is a pattern recognition receptor (PRR) recognizing chemically synthesized long dsRNA. FIG. 2.

Figure 3:
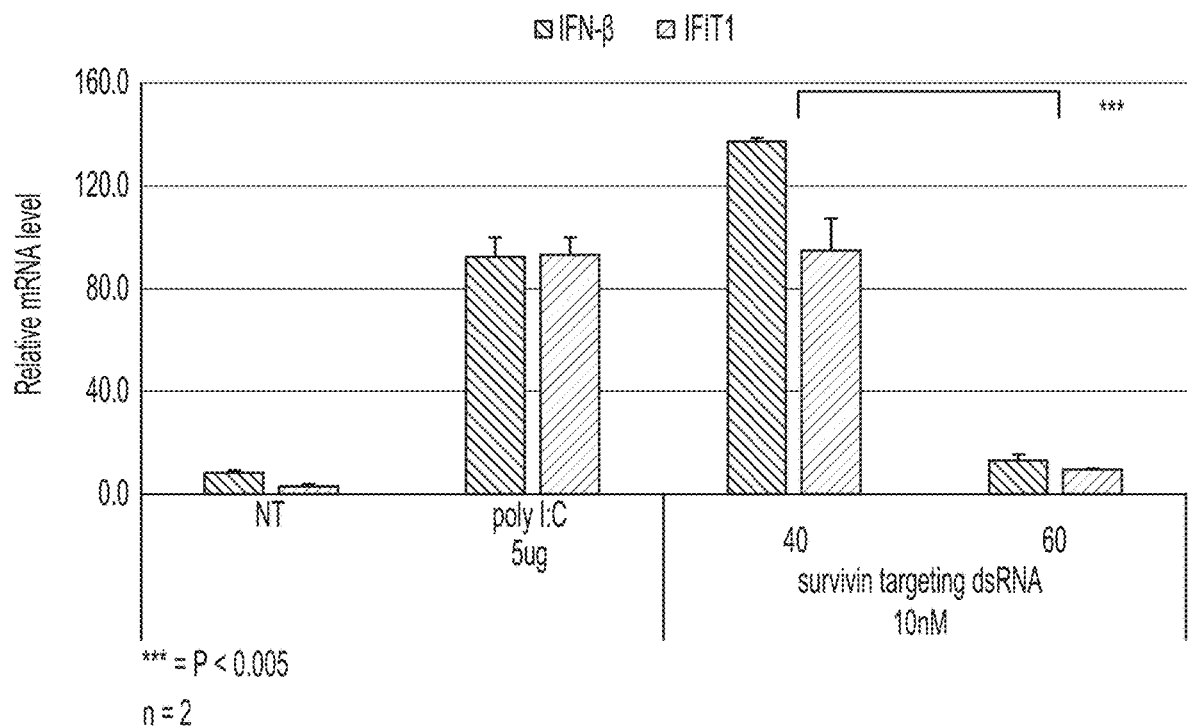
FIG. 3 is a graph showing gene expression of IFN-β and IFIT1(ISG56) in cells transfected with blunt-ended dsRNAs targeting the survivin gene with lengths of 40 bp and 60 bp.

FIG. 3 shows that IFN-β and IFIT1(ISG56) gene expression are not upregulated by transfection with 60 bp dsRNA. This result indicates that the reason ISG54 is not upregulated by 60 bp dsRNA is not due to translation inhibition by PKR but rather because the 60 bp dsRNA does not activate innate immune system.

Figure 4:
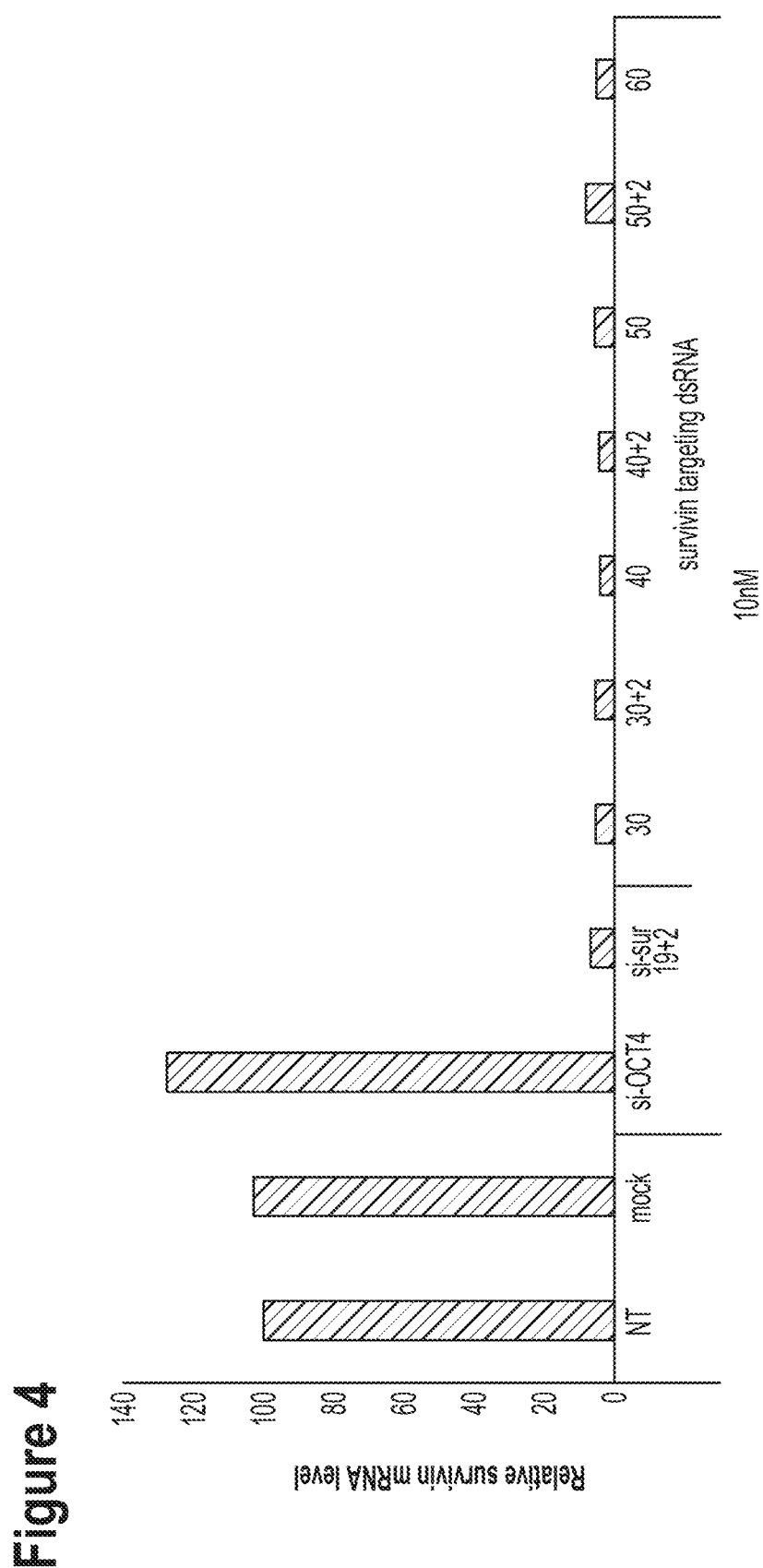
FIG. 4 is a graph showing that survivin targeting dsRNAs having 30 bp, 30+2, 40 bp, 40+2, 50 bp, 50+2, and 60 bp knock-down the target survivin mRNA compared to conventional siRNA for survivin.

FIG. 4 shows that the 30 bp, 30+2, 40 bp, 40+2, 50 bp, 50+2, and 60 bp survivin targeting dsRNAs disclosed above can silence survivin gene expression with the same efficacy as conventional siRNA for survivin (si-sur 19+2).

EQUIVALENTS

While the invention has been described in connection with specific embodiments thereof, it will be understood that it is capable of further modifications and this application is intended to cover any variations, uses, or adaptations of the invention following, in general, the principles of the inven-

What is claimed is:

1. A composition comprising long double-stranded RNA (ldRNA) capable of triggering gene silencing via an RNA interference (RNAi) mechanism, wherein
the ldRNA consists of two substantially complementary RNA strands and comprises at least one guide sequence complementary to one or more target mRNAs, and
each of the RNA strands is in the range of 40 to 80 nucleotides and has an overhang on a 3' end, wherein the ldRNA comprises one or more phosphorothioate linkages.

2. The composition of claim 1, wherein each of the RNA strands is in the range of 45 to 60 nucleotides.

3. The composition of claim 1, wherein each of the RNA strands is in the range of 50 to 60 nucleotides.

4. The composition of claim 1, wherein the ldRNA comprises two or more sequences of at least 8 base pair (bp) having a guide sequence complementary to the same target mRNA.

5. The composition of claim 1, wherein the ldRNA comprises two or more sequences of at least 8 bp having a guide sequence complementary to different target mRNAs.

6. The composition of claim 1, wherein an end of the ldRNA comprises a 5' end of an antisense sequence complementary to the target mRNAs.

7. The composition of claim 1, wherein the sequences complementary to the target mRNAs are each independently selected from sequences that are 8 to 50 nucleotides in length.

8. The composition of claim 1, wherein the target mRNAs are viral mRNAs.

9. The composition of claim 1, wherein the target mRNAs are involved in multiple pathways critical for cancer cell growth and survival, function in the same signal transduction pathway, or function in two or more signal transduction pathways that emanate from a common signal.

10. The composition of claim 1, wherein the target mRNAs encode an enzyme, a transcription factor, a secreted signaling protein, a signal transduction protein, a kinase or phosphatase, a cellular receptor or an ion channel, or a secreted protein.

11. The composition of claim 1, wherein the overhang is a di-nucleotide overhang.

12. The composition of claim 1, wherein the ldRNA causes little or no activation of an antiviral response.

13. A method for inhibiting gene expression comprising administering the composition of claim 1 to a mammalian cell, tissue, or animal.

14. A method of reducing the expression of one or more mRNAs, comprising administering the composition of claim 1 to a mammalian cell, tissue, or animal.

15. A pharmaceutical composition comprising the composition of claim 1, and a pharmaceutically acceptable carrier.

16. The composition of claim 1, wherein the ldRNA is encapsulated in liposomes.

17. The composition of claim 1, wherein the ldRNA is formulated for administration by inhalation, intravenous injection, subcutaneous injection, intradermal injection, intramuscular injection, intraocular injection, intratumoral injection, or other forms of parenteral administration.

18. The composition of claim 1, wherein the ldRNA is formulated for topical administration.

19. The composition of claim 1, wherein the ldRNA comprises a lipophilic conjugate selected from cholesterol, tocopherol, cholestene, cholestane, cholestadiene, bile acid, cholic acid, deoxycholic acid, dehydrocholic acid, and a long-chain fatty acid having 10 or more carbon atoms.

* * * * *